US006197971B1

(12) United States Patent
Kulkarni et al.

(10) Patent No.: US 6,197,971 B1
(45) Date of Patent: Mar. 6, 2001

(54) PROCESS FOR THE MANUFACTURE OF SUBSTITUTED TRIAZOLINONES

(75) Inventors: Shekhar V. Kulkarni, Shawnee; Vidyanatha A. Prasad, Leawood; Vijay C. Desai, Shawnee; Eric Rivadeneira, Overland Park, all of KS (US); Klaus Jelich, Wuppertal (DE)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/472,482

(22) Filed: Dec. 27, 1999

(51) Int. Cl.$^7$ ................................................. C07D 249/12
(52) U.S. Cl. ......................................................... 548/263.6
(58) Field of Search ............................................ 548/263.6

(56) References Cited

U.S. PATENT DOCUMENTS

| | | | |
|---|---|---|---|
| 5,594,148 | 1/1997 | Wroblowsky et al. | 548/263.6 |
| 5,599,945 | 2/1997 | Wroblowsky et al. | 549/263.6 |
| 5,606,070 | 2/1997 | Wroblowsky et al. | 548/263.6 |
| 5,708,183 | 1/1998 | Wroblowsky | 548/263.8 |
| 5,912,354 | 6/1999 | Desai et al. | 548/263.8 |
| 5,917,050 | 6/1999 | Conrad et al. | 548/263.6 |

*Primary Examiner*—Laura L. Stockton
(74) *Attorney, Agent, or Firm*—Joseph C. Gil

(57) ABSTRACT

The present invention relates to a process for manufacturing substituted triazolinones, which are intermediates in the preparation of herbicidally active compounds. In particular, this invention relates to the alkylation of a non-alkylated triazolinone intermediate product, wherein the improvement comprises conducting the alkylation reaction under pH controlled conditions. In a preferred embodiment, the invention relates to the preparation of a 5-alkoxy(or aryloxy)-2,4-dihydro-3H-1,2,4-triazol-3-one, and the alkylation of this non-alkylated triazolinone intermediate product, to produce a 5-alkoxy(or aryloxy)-4-alkyl-2,4-dihydro-3H-1,2,4-triazol-3-one.

27 Claims, No Drawings

PROCESS FOR THE MANUFACTURE OF SUBSTITUTED TRIAZOLINONES

TECHNICAL FIELD OF THE INVENTION

The present invention relates to a process for manufacturing substituted triazolinones, which are intermediates in the preparation of herbicidally active compounds. In particular, this invention relates to the alkylation of a non-alkylated triazolinone intermediate product, wherein the improvement comprises conducting the alkylation reaction under pH controlled conditions. In this context the term "alkylation" represents a generic term and thus, includes the use of alkylating agents having an alkyl group, an alkenyl group, an alkynyl group, a cycloalkyl group, a cycloalkylalkyl group, an aryl group or an arylalkyl group.

In a preferred embodiment, the invention relates to the preparation of a 5-alkoxy(or aryloxy)-2,4-dihydro-3H-1,2,4-triazol-3-one, and the alkylation of this non-alkylated triazolinone intermediate product to produce a 5-alkoxy(or aryloxy)-4-alkyl-2,4-dihydro-3H-1,2,4-triazol-3-one.

BACKGROUND OF THE INVENTION

Triazolinones are well known in the art, as are processes for their preparation and use as herbicides. U.S. Pat. No. 5,708,183 describes a process for the preparation of substituted triazolinones by reacting triazolinethiones with methyl iodide, in the presence of an acid binding agent, and then heating the alkylthiodiazole derivative with hydrogen peroxide in the presence of acetic acid. U.S. Pat. No. 5,912,354 discloses a process for the preparation of substituted aminotriazolinones, which includes reacting an oxadiazolinone with hydrazine hydrate in the absence of a solvent. U.S. Pat. No. 5,917,050 describes a process for the preparation of alkoxytriazolinones by reacting thioimidodicarboxylic diesters with hydrazine, hydrazine hydrate or an acid adduct of hydrazine, in the presence of a diluent and a basic reaction auxiliary.

Further, U.S. Pat. Nos. 5,606,070; 5,599,945; and 5,594,148; each describes a process for the preparation of alkoxytriazolinones which includes reacting iminothiocarbonic diesters with carbazinic esters, and then subjecting the resultant semicarbazide derivatives to a cyclizing condensation reaction.

However, these prior art processes produce triazolinones in unsatisfactory yield and purity. Thus, there is a need in the art for a process to manufacture substituted triazolinones in high yield and purity.

BRIEF SUMMARY OF INVENTION

The present invention is related to a process for the preparation of a substituted triazolinone. The process includes the reaction of a thionocarbamate of the following general formula (I)

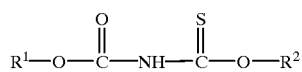
(I)

wherein
R$^1$ represents an unsubstituted or substituted alkyl, arylalkyl or aryl, and
R$^2$ represents an unsubstituted or substituted alkyl, alkenyl, alkynyl, cycloalkyl, cycloalkylalkyl, aryl or arylalkyl, with hydrazine, hydrazine hydrate or an acid adduct of hydrazine, to produce a triazolinone intermediate product of the following general formula (II)

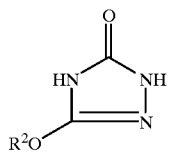
(II)

wherein
R$^2$ is as defined above.

The intermediate product of the general formula (II) is then reacted under pH controlled reaction conditions with an alkylating agent of the following general formula (III)

R$^3$—X (III)

wherein
X represents a halogen, —O—SO$_2$—O—R$^3$, or —O—CO—O—R$^3$, and
R$^3$ represents an unsubstituted or substituted alkyl, alkenyl, alkynyl, cycloalkyl, cycloalkylalkyl, aryl or arylalkyl, in the presence of a solvent and a base, to produce a substituted triazolinone of the following general formula (IV)

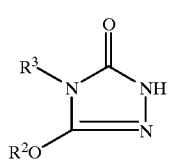
(IV)

wherein
R$^2$ and R$^3$ are as defined above.

DETAILED DESCRIPTION OF THE INVENTION

The present invention is related to a process for the preparation of a substituted triazolinone by the alkylation of a non-alkylated triazolinone intermediate product. In this context, the term "alkylation" is used as a generic term and thus, expressly includes the definition of R$^3$ provided below. The process includes the reaction of a thionocarbamate of the following general formula (I)

(I)

wherein
R$^1$ represents an unsubstituted or substituted alkyl, arylalkyl or aryl, and
R$^2$ represents an unsubstituted or substituted alkyl, alkenyl, alkynyl, cycloalkyl, cycloalkylalkyl, aryl or arylalkyl, with hydrazine, hydrazine hydrate or an acid adduct of hydrazine, to produce a triazolinone intermediate product of the following general formula (II)

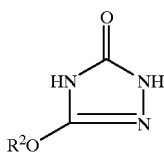

(II)

wherein
R² is as defined above.

The intermediate product of the general formula (II) is then reacted under pH controlled reaction conditions with an alkylating agent of the following general formula (III)

R³—X  (III)

wherein
X represents a halogen, —O—SO₂—O—R³, or —O—CO—O—R³, and
R³ represents an unsubstituted or substituted alkyl, alkenyl, alkynyl, cycloalkyl, cycloalkylalkyl, aryl or arylalkyl, in the presence of a solvent and a base, to produce a substituted triazolinone of the following general formula (IV)

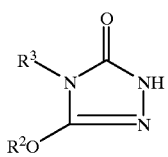

(IV)

wherein
R² and R³ are as defined above.

In a preferred embodiment of the invention,
R¹ represents an alkyl group having 1 to 4 carbon atoms, a benzyl group or a phenyl group, and
R² represents an alkyl group, an alkenyl group or an alkynyl group having in each case up to 6 carbon atoms, and each of which is unsubstituted or substituted by cyano, halogen or $C_1$–$C_4$-alkoxy, or
represents a cycloalkyl group having 3 to 6 carbon atoms or a cycloalkylalkyl group having 3 to 6 carbon atoms in the cycloalkyl moiety and 1 to 4 carbon atoms in the alkyl moiety, each of which is unsubstituted or substituted by halogen or $C_1$–$C_4$-alkyl, or
represents an aryl group having 6 or 10 carbon atoms or an arylalkyl group having 6 or 10 carbon atoms in the aryl moiety and 1 to 4 carbon atoms in the alkyl moiety, each of which is unsubstituted or substituted by carboxyl, nitro, cyano, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl, and
R³ represents an alkyl, alkenyl or alkynyl, each of which has up to 6 carbon atoms and each of which is unsubstituted or substituted by cyano, halogen or $C_1$–$C_4$-alkoxy, or
represents a cycloalkyl having 3 to 6 carbon atoms or a cycloalkylalkyl having 3 to 6 carbon atoms in the cycloalkyl moiety and 1 to 4 carbon atoms in the alkyl moiety, each of which is unsubstituted or substituted by halogen or $C_1$–$C_4$-alkyl, or
represents an aryl having 6 to 10 carbon atoms or an arylalkyl having 6 or 10 carbon atoms in the aryl moiety and 1 to 4 carbon atoms in the alkyl moiety, each of which is unsubstituted or substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl.

More preferably,
R² represents methyl, ethyl, n- or i-propyl, n-, i-, s-, or t-butyl, each of which is unsubstituted or substituted by cyano, fluorine, chlorine or bromine, methoxy or ethoxy, or
represents propenyl, butenyl, propinyl or butinyl, each of which is unsubstituted or substituted by cyano, fluorine, chlorine or bromine, or
represents cyclopropyl or cyclopropylmethyl, each of which is unsubstituted or substituted by fluorine, chlorine, bromine, methyl or ethyl, or
represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl, and
R³ represents methyl, ethyl, n- or i-propyl or n-, i-, s- or t-butyl, each of which is unsubstituted or substituted by cyano, fluorine, chlorine or bromine, methoxy or ethoxy, or
represents propenyl, butenyl, propinyl or butinyl, each of which is unsubstituted or substituted by cyano, fluorine, chlorine or bromine, or
represents cyclopropyl, cyclobutyl or cyclopropylmethyl, each of which unsubstituted or substituted by fluorine, chlorine, bromine, methyl or ethyl, or
represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl.

Most preferably,
R¹ and R² each represents methyl, n- or i-propyl, and
R³ represents methyl.

The process of the invention may be conducted as a one pot process, without isolation of the intermediate product of formula (II).

The process according to the invention is generally carried out at atmospheric pressure. However, it is also possible to conduct the process under elevated or reduced pressure.

The reaction of a thionocarbamate with hydrazine, hydrazine hydrate or an acid adduct of hydrazine, is carried out at a temperature of from about −10° C. to about 95° C., and preferably at a temperature of from about 0° C. to about 60° C. Examples of suitable acid adducts of hydrazine include hydrazine acetate, hydrazine hydrochloride, and hydrazine sulfate.

In an embodiment of the invention, the reaction of the thionocarbamate with hydrazine, hydrazine hydrate or an acid adduct of hydrazine, is carried out in the presence of a base, a solvent, or mixtures thereof.

Suitable bases include customary inorganic or organic bases or acid acceptors. These include alkali metal or alkaline earth metal acetates, amides, carbonates, bicarbonates, hydrides, hydroxides, or alkoxides such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide, and also basic organic nitrogen compounds such as trimethylamine, triethylamine, tripropylamine, tributylamine, ethyl diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Suitable solvents include aliphatic, alicyclic or aromatic, unhalogenated or halogenated hydrocarbons such as, for example, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; ketones such as acetone, butanone, or methyl isobutyl ketone; nitriles such as acetonitrile, propionitrile or butyronitrile; amides such as N,N-dimethylformamide, N,N-dimethylacetamide, N-methyl-formanilide, N-methyl-pyrrolidone or hexamethylphosphoric triamide; esters such as methyl acetate or ethyl acetate; sulfoxides such as dimethyl sulfoxide; alcohols such as methanol, ethanol, n- or i-propanol, n-, i-, s- or t-butanol, ethylene glycol monomethyl ether, ethylene glycol monoethyl ether, diethylene glycol monomethyl ether, diethylene glycol monoethyl ether; water; and mixtures thereof.

Preferred solvents include water, methanol, propanol, and a commercially available mixture of xylenes containing ethylbenzene, ortho-xylene, para-xylene and meta-xylene.

In an embodiment of the invention, the reaction of a thionocarbamate with hydrazine hydrate is carried out in a mixture of water and methanol, or a mixture of water, propanol, and xylenes.

In another embodiment, a nitrogen flow is maintained through the reaction mixture for the purpose of removing the $H_2S$ formed in the reaction.

Further, in another embodiment of the invention, benzyl chloride is added to the reaction mixture containing the thionocarbamate and hydrazine, hydrazine hydrate or acid adduct of hydrazine, to improve the purity of the alkylated triazolinone product of formula (IV). The benzyl chloride is added to the reaction mixture at a temperature of from about –10° C. to about 95° C., in an amount such that the benzyl chloride is from about 0.1% to about 10% by mole of the mixture; and preferably from about 3% to about 5% by mole.

In an embodiment of the invention, a base is added to the reaction mixture following the completion of the reaction between the thionocarbamate and hydrazine, hydrazine hydrate or acid adduct of hydrazine. The base is added in an amount such that the pH of the resulting mixture is from about 8.0 to about 12.0. Suitable bases include alkali metal or alkaline earth metal salts of an acid having a pKa value of 5 or higher. Examples of such bases include alkali metal or alkaline earth metal hydroxides, carbonates, bicarbonates, and alkoxides. In a preferred embodiment, the base is potassium hydroxide.

In the process of the invention, following the completion of the reaction between the thionocarbamate and hydrazine, hydrazine hydrate or acid adduct of hydrazine, an alkylating agent is added to the reaction mixture. The alkylation of the intermediate compound of the formula (II) proceeds with high selectivity on the N atom in the 4-position. In this context, the terms "alkylation" and "alkylating agent" (formula III) are used as generic terms and thus, expressly include the above definition of $R^3$.

The alkylation reaction is carried out at a temperature of from about –10° C. to about 95° C., and preferably at a temperature of from about 20° C. to about 70° C. As a result of adding the alkylating agent, the pH of the reaction mixture decreases to a value of from about 7.0 to about 9.0. The reaction mixture is then maintained at a pH of from about 7.0 to about 9.0, preferably from about 7.5 to about 8.5, and most preferably from about 7.9 to about 8.1, by the addition of a base to the mixture as necessary.

The reaction time for the alkylation step corresponds to the time that is necessary for the pH of the reaction mixture to remain stable between 7.0 and 9.0, and preferably between 7.5 and 8.5, without the addition of a base.

The base for use in the alkylation step of the present invention includes the conventional inorganic or organic bases. These include, for example, the hydrides, hydroxides, amides, alcoholates, acetates, carbonates, or hydrogen carbonates of alkaline earth metals or alkali metals such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate, or ammonium carbonate, and also basic organic nitrogen compounds such as trimethylamine, triethylamine, tributylamine, N,N-dimethylaniline, N,N-dimethyl-benzylamine, pyridine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Suitable alkylating agents for use in the process of the present invention include compounds of the general formula (III) as defined above. A preferred alkylating agent is dimethyl sulfate. The alkylation reaction is carried out in the presence of a solvent.

Suitable solvents for use in the alkylation reaction of the present invention include aliphatic, alicyclic or aromatic, optionally halogenated hydrocarbons such as, for example, benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran or ethylene glycol dimethyl ether or ethylene glycol diethyl ether; ketones such as acetone, butanone, or methyl isobutyl ketone; nitriles such as acetonitrile, propionitrile or benzonitrile; amides such as N,N-dimethylformamide, N,N-dimethylacetamide, N-methylformanilide, N-methyl-pyrrolidone or hexamethylphosphoric triamide; esters such as methyl acetate or ethyl acetate, sulfoxides such as dimethyl sulfoxide, alcohols such as methanol, ethanol, n- or i-propanol, n-, i-, s-, or t-butanol, ethylene glycol monomethyl ether, ethylene glycol monoethyl ether, diethylene glycol monomethyl ether, diethylene glycol monoethyl ether; water and mixtures thereof. Preferred solvents include methyl isobutyl ketone, methanol, propanol, water and a commercially available mixture of xylenes containing ethylbenzene, ortho-xylene, para-xylene, and meta-xylene.

In an embodiment of the invention, the alkylation reaction is carried out in the presence of a mixture of water, methanol and methyl isobutyl ketone, or a mixture of water, propanol and xylenes.

In another embodiment of the invention, the substituted triazolinone product of the general formula (IV) is isolated as a hydrate at the end of the alkylation reaction.

Further, in a preferred embodiment, 5-methoxy-4-methyl-2,4-dihydro-3H-1,2,4-triazol-3-one (MMT) is produced by methylating 5-methoxy-2,4-dihydro-3H-1,2,4-triazol-3-one (HMT) in a mixture of MIBK, methanol, and water. The molar ratio of HMT to MIBK is from about 1.0:2.0 to about 1.0:3.5, and preferably about 1.0:2.8. The molar ratio of HMT to methanol is from about 1.0:5.0 to about 1.0:15.0, and preferably about 1.0:9.5. The molar ratio of HMT to water is from about 1.0:3.0 to about 1.0:6.0, and preferably about 1.0:4.8.

Moreover, in a preferred embodiment, 5-propoxy-4-methyl-2,4-dihydro-3H-1,2,4-triazol-3-one (PMT) is produced by methylating 5-propoxy- 2,4-dihydro-3H-1,2,4-triazol-3-one (HPT) in a mixture of xylenes, propanol, and water. The reaction mixture contains an aqueous phase and an organic phase. The aqueous phase (lower phase) is discarded and the PMT is recovered from the organic phase (upper phase) at a temperature of 60° C., in the presence of propanol and methanol. The molar ratio of HPT to xylenes is from about 1.0:2.0 to about 1.0:4.0, and preferably about 1.0:3.0. The molar ratio of HPT to propanol is from about 1.0:2.0 to about 1.0:6.0, and preferably about 1.0:4.0. The molar ratio of HPT to water is from about 1.0:3.0 to about 1.0:9.0, and preferably about 1.0:6.1.

The invention is further illustrated but is not intended to be limited by the following examples in which all parts and percentages are by weight unless otherwise specified.

EXAMPLES

Example 1

The Preparation of HMT

To a chilled (i.e., about 0° C.) solution containing 399.0 grams (2.68 moles) of N-methoxycarbonyl-O-methylthionocarbamate (MTC) and 710 grams of methanol, was added 17.8 grams (0.143 mole) of 45% aqueous potassium hydroxide and 40.0 grams of water. At a temperature of about 0° C., 133.8 grams (2.65 moles) of 64% hydrazine hydrate were added to the reaction mixture over a period of about 2 hours at a uniform rate. A net subsurface nitrogen flow (to help remove the H$_2$S formed in the reaction) was maintained through the reaction mixture. The reaction mixture was stirred at a temperature of about 0° C. for about 4 hours. The mixture was then heated to a temperature of about 40° C. over a time period of about 2 hours. At a temperature of about 40° C., 17.1 grams (0.135 mole) of benzyl chloride were added to the reaction mixture and the mixture was maintained at this temperature for about 1 hour. The reaction mixture was then heated to a temperature of about 50° C. over a period of about 1 hour and the mixture was maintained at this temperature for about 2 hours. The reaction mixture contained about 262 grams (2.28 moles, 85% yield based on MTC) of 5-methoxy-2,4-dihydro-3H-1,2,4-triazol-3-one (HMT) in a mixture of methanol (MeOH) and water.

At this point, the HMT slurry was either further reacted to produce an 5-alkoxy-4-methyl-2,4-dihydro-3H-1,2,4-triazol-3-one (e.g., Example 3), or the pure HMT was isolated from the reaction mixture. To isolate the pure HMT, the reaction mixture was cooled to a temperature of about 0° C., filtered under vacuum and the filter cake was washed with 2 X 50 ml of cold (about 0° C.) methanol. The filter cake was then dried in a vacuum oven at a temperature of about 50° C. for about 16 hours to obtain 223.6 grams of HMT (96.5% purity and 70.0% yield based on MTC).

Example 2

The Preparation of HPT

To a solution containing 587.0 grams (2.86 moles) of N-propoxycarbonyl-O-propylthionocarbamate (PTC) and 240 grams of propanol, was added 280 grams of xylenes (i.e., a commercially available mixture of ethylbenzene, ortho-xylene, para-xylene and meta-xylene), 70.0 grams of water, and 4.2 grams (0.03 mole) of 45% aqueous potassium hydroxide. The reaction mixture was then cooled to a temperature of about 0° C. At a temperature of about 0° C., 146.0 grams (2.95 moles) of 64% hydrazine hydrate were added to the reaction mixture over a period of about 2 hours at a uniform rate. A net subsurface nitrogen flow (to help remove the H$_2$S formed in the reaction) was maintained through the reaction mixture. Following addition of the hydrazine hydrate, the reaction mixture was heated to a temperature of about 20° C. and stirred for about 3 hours. The mixture was then heated to a temperature of about 50° C. over a time period of about 2 hours. The reaction mixture was cooked at a temperature of about 50° C. for about I hour. The reaction mixture was then diluted with 525 grams of xylenes. This slurry contained about 348 grams (2.43 moles, 85% yield based on PTC) of 5-propoxy-2,4-dihydro-3H-1, 2,4-triazol-3-one (HPT) in a mixture of xylenes, propanol and water.

At this point, the HPT was further reacted to produce 5-propoxy-4-methyl-2,4-dihydro-3H-1,2,4-triazol-3-one (e.g., Example 4).

Example 3

Preparation of MMT Hydrate from HMT Slurry

To a HMT slurry (e.g., as prepared in Example 1), which contained 262 grams (2.28 moles) of HMT in a mixture of methanol and water, was added 45% aqueous potassium hydroxide (KOH) solution at a temperature of about 50° C., over a time period of about 30 minutes. The KOH solution was added in an amount such that the pH of the reaction mixture was increased to about 10.0. About 650 grams of methyl isobutyl ketone (MIBK) were then added to the reaction mixture, and the mixture was cooled to room temperature (i.e., about 25° C.). About 446 grams (3.54 moles) of dimethyl sulfate were then added to the mixture over a period of about 2 hours, while maintaining the temperature of the mixture from about 25° C. to about 30° C. As the dimethyl sulfate was added, the pH of the reaction mixture decreased. The pH of the mixture was maintained between about 7.9 and about 8.1 by the simultaneous addition of 45% aqueous KOH solution. Following addition of the dimethyl sulfate, the temperature of the reaction mixture was increased to about 60° C. over a time period of about 4 hours, while maintaining the pH between about 7.9 and about 8.1.

The reaction mixture was cooked at about 60° C. until the pH was stable; i.e., the point at which the addition of aqueous KOH was not necessary to maintain the pH between about 7.9 and about 8.1.

A fractional distillation of the reaction mixture was then conducted under reduced pressure to remove the methanol, and isolate the 5-methoxy-4-methyl-2,4-dihydro-3H-1,2,4-triazol-3-one (M MT) product as a hydrate. About 680 grams of water were added to the residue and heated to a temperature of about 75° C. to dissolve the MMT. The mixture was then cooled to a temperature of about 0° C. over a time period of about 4 hours, and stirred for about 1 hour. The resulting two phase slurry was filtered, and then washed with 280 grams of warm MIBK and 280 grams of ice cold water. The filter cake was dried at room temperature for about 8 hours under a 200 mm vacuum, to obtain 261 grams of MMT hydrate (1.74 moles, purity of 98% as hydrate, and yield of 76% based on HMT).

Example 4
Preparation of PMT Solution in Xylenes from HPT slurry in Xylenes/Propanol/Water To a HPT slurry (e.g., as prepared in Example 2), which contained 348 grams (2.43 moles) of HPT in a mixture of xylenes, propanol and water, was added 45% aqueous potassium hydroxide (KOH) solution at a temperature of about 30° C., over a time period of about 30 minutes. The KOH solution was added in an amount such that the pH of the reaction mixture was increased to about 10.0. About 480 grams (3.77 moles) of dimethyl sulfate were then added to the mixture over a period of about 2 hours, while maintaining the temperature of the mixture from about 25° C. to about 30° C. As the dimethyl sulfate was added, the pH of the reaction mixture decreased. The pH of the mixture was maintained between about 7.9 and about 8.1 by the simultaneous addition of 45% aqueous KOH solution. Following addition of the dimethyl sulfate, the temperature of the reaction mixture was increased to about 60° C. over a time period of about 4 hours, while maintaining the pH between about 7.9 and about 8.1.

The reaction mixture was cooked at about 60° C. until the pH was stable; i.e., the point at which the addition of aqueous KOH was not necessary to maintain the pH between about 7.9 and about 8.1. Stirring of the reaction mixture was stopped and the mixture separated into two phases. The aqueous phase (lower phase) was discarded and the organic phase (upper phase) was subjected to distillation under reduced pressure to remove the methanol, dipropyl ether, propanol and water. The residue, which consisted of crude 5-propoxy-4-methyl-2,4-dihydro- 3H-1,2,4-triazol-3-one (PMT) in xylenes, was diluted with fresh anhydrous xylenes to adjust its concentration to about 13% with respect to PMT. At this point the PMT solution contained 319 grams (2.03 moles) of PMT in 2455 grams of total solution. The solvent-free purity of PMT was 82% and the yield was 83.5% based on HPT.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a substituted triazolinone comprising the steps of:

a) reacting a thionocarbamate of the following general formula (I)

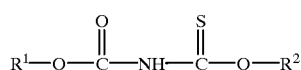

(I)

wherein
$R^1$ represents an unsubstituted or substituted alkyl, arylalkyl or aryl, and
$R^2$ represents an unsubstituted or substituted alkyl, alkenyl, alkynyl, cycloalkyl, cycloalkylalkyl, aryl or arylalkyl,
with hydrazine, hydrazine hydrate, or an acid adduct of hydrazine, to produce a triazolinone intermediate product of the following general formula (II)

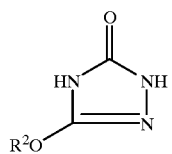

(II)

wherein $R^2$ is as defined above; and b) reacting the intermediate product of formula (II) in step a) under pH controlled conditions of from about pH 7.0 to about pH 9.0 with an alkylating agent of the following general formula (III)

(III)

wherein
X represents a halogen, $-O-SO_2-O-R^3$, or $-O-CO-O-R^3$, and
$R^3$ represents an unsubstituted or substituted alkyl, alkenyl, alkynyl, cycloalkyl, cycloalkylalkyl, aryl or arylalkyl,
in the presence of a solvent and a base, to produce a substituted triazolinone of the following general formula (IV)

(IV)

wherein $R^2$ and $R^3$ are as defined above.

2. The process of claim 1 wherein the reaction in step a) is carried out at a temperature of from about −10° C. to about 95° C.

3. The process of claim 1 wherein the reaction in step a) is carried out at a temperature of from about 0° C. to about 60° C.

4. The process of claim 1 wherein the reaction in step a) is carried out in the presence of a compound selected from the group consisting of a base, a solvent, and mixtures thereof.

5. The process of claim 4 wherein the base is selected from the group consisting of alkali metal and alkaline earth metal acetates, amides, carbonates, bicarbonates, hydrides, hydroxides, alkoxides, and basic organic nitrogen compounds.

6. The process of claim 4 wherein the solvent is selected from the group consisting of aliphatic, alicyclic and aromatic, unhalogenated and halogenated hydrocarbons, ethers, ketones, nitriles, esters, sulfoxides, amides, alcohols, water and mixtures thereof.

7. The process of claim 1 wherein the reaction in step a) is carried out in the presence water, methanol, and potassium hydroxide.

8. The process of claim 1 wherein the reaction in step a) is carried out in the presence of water, propanol, xylenes, and potassium hydroxide.

9. The process of claim 1 wherein a nitrogen flow is maintained through the reaction mixture.

10. The process of claim 1 wherein benzyl chloride is added to the reaction mixture in step a).

11. The process of claim 10 wherein the benzyl chloride is added in an amount such that the benzyl chloride is from about 0.1% to about 10% by mole of the reaction mixture.

12. The process of claim 1 wherein the reaction in step b) is carried out at a temperature of from about −10° C. to about 95° C.

13. The process of claim 1 wherein the reaction in step b) is carried out at a temperature of from about 20° C. to about 70° C.

14. The process of claim 1 wherein the base recited in step b) is potassium hydroxide.

15. The process of claim 1 wherein the alkylating agent is dimethyl sulfate.

16. The process of claim 1 wherein the solvent recited in step b) is selected from the group consisting of aliphatic, alicyclic and aromatic, unhalogenated or halogenated hydrocarbons, ethers, ketones, nitriles, esters, sulfoxides, amides, alcohols, water and mixtures thereof.

17. The process of claim 1 wherein the solvent is a mixture of methyl isobutyl ketone, methanol and water.

18. The process of claim 1 wherein the solvent is a mixture of xylenes, propanol and water.

19. The process of claim 1 wherein steps a) and b) are carried out via a one-pot process without separation of the intermediate product of formula (II).

20. The process of claim 1 wherein the triazolinone product of formula (IV) is 5-methoxy-4-methyl-2,4-dihydro-3H-1,2,4-triazol-3-one (MMT).

21. The process of claim 20 further comprising the step of isolating the 5-methoxy-4-methyl-2,4-dihydro-3H-1,2,4-triazol-3-one (MMT) as a monohydrate.

22. The process of claim 1 wherein the triazolinone product of formula (IV) is 5-propoxy-4-methyl-2,4-dihydro-3H-1,2,4-triazol-3-one (PMT).

23. The process of claim 1 wherein the pH of the reaction mixture is from about 7.5 to about 8.5.

24. The process of claim 1 wherein the pH of the reaction mixture is from about 7.9 to about 8.1.

25. The process of claim 22 further comprising the step of recovering the PMT by separating it from an organic phase of the reaction mixture at a temperature of 60° C., in the presence of propanol and methanol.

26. The process of claim 1 further comprising the step of adding a base to the reaction mixture of step a) prior to adding the alkylating agent in step b), in an amount such that the pH of the reaction mixture is from about 8.0 to about 12.0.

27. The process of claim 1 wherein the base recited in step b) is selected from the group consisting of alkali metal and alkaline earth metal acetates, amides, carbonates, bicarbonates, hydrides, hydroxides, alkoxides, and basic organic nitrogen compounds.

* * * * *